(12) United States Patent
Dreyer et al.

(10) Patent No.: US 10,863,886 B2
(45) Date of Patent: Dec. 15, 2020

(54) ROTATABLE INTRODUCERS

(71) Applicant: UVision360, Inc., Raleigh, NC (US)

(72) Inventors: Erich Dreyer, Durham, NC (US);
David Robinson, Schaumburg, IL (US);
Allison London Brown, Durham, NC (US)

(73) Assignee: UVision360, Inc., Raleigh, NC (US)

( * ) Notice: Subject to any disclaimer, the term of this patent is extended or adjusted under 35 U.S.C. 154(b) by 0 days.

(21) Appl. No.: 16/402,839

(22) Filed: May 3, 2019

(65) Prior Publication Data

US 2020/0345212 A1 Nov. 5, 2020

(51) Int. Cl.
*A61B 1/00* (2006.01)
*A61B 1/018* (2006.01)
*A61B 1/015* (2006.01)

(52) U.S. Cl.
CPC ...... *A61B 1/00154* (2013.01); *A61B 1/00103* (2013.01); *A61B 1/00112* (2013.01); *A61B 1/015* (2013.01); *A61B 1/018* (2013.01)

(58) Field of Classification Search
CPC ... A61B 1/0105; A61B 1/00135; A61B 1/018; A61B 2017/003; A61B 2017/3445; A61B 1/00154
USPC .......................................................... 600/105
See application file for complete search history.

(56) References Cited

U.S. PATENT DOCUMENTS

| | | | |
|---|---|---|---|
| 5,231,989 A | 8/1993 | Middleman et al. | |
| 5,483,951 A | 1/1996 | Frassica et al. | |
| 5,611,769 A | 3/1997 | Monroe | |
| 5,645,519 A * | 7/1997 | Lee | A61B 1/2676 600/114 |
| 5,823,940 A | 10/1998 | Newman | |
| 5,961,486 A | 10/1999 | Twardowski et al. | |
| 6,110,103 A | 8/2000 | Donofrio | |
| 6,371,909 B1 | 4/2002 | Hoeg et al. | |
| 6,419,626 B1 | 7/2002 | Yoon | |
| 6,482,169 B1 | 11/2002 | Kuhle | |
| 6,572,631 B1 | 6/2003 | McCartney | |

(Continued)

FOREIGN PATENT DOCUMENTS

| | | |
|---|---|---|
| CA | 2593731 C | 1/2015 |
| DE | 19752430 A1 | 7/1999 |

(Continued)

*Primary Examiner* — Alexandra L Newton
(74) *Attorney, Agent, or Firm* — Mintz Levin Cohn Ferris Glovsky and Popeo, P.C.

(57) ABSTRACT

Various rotatable shafts and linkage mechanisms configured to allow imaging and access to tissue within a body are provided. In an exemplary embodiment, an introducer system has a rotatable sheath and a linkage that can rotatably engage each other. The rotatable sheath has a distal portion extending at a non-zero angle relative to a proximal portion thereof. The linkage has an exit lumen on its distal end and a plurality of entry lumens on its proximal end. The linkage merges the plurality of entry lumens into the exit lumen, and the exit lumen is aligned with the rotatable sheath upon engagement. Fluid and/or surgical instruments can thus be passed from the plurality of entry lumens of the linkage, through the exit lumen of the linkage, and into the rotatable sheath. The linkage and the rotatable sheath can both receive an imaging device therethrough.

18 Claims, 10 Drawing Sheets

(56) References Cited

U.S. PATENT DOCUMENTS

| | | | |
|---|---|---|---|
| 6,749,580 B2 | 6/2004 | Work et al. | |
| 6,761,684 B1 | 7/2004 | Speier | |
| 6,863,651 B2 | 3/2005 | Remijan et al. | |
| 6,926,005 B1* | 8/2005 | Colman | A61M 16/08 128/202.27 |
| 6,958,035 B2 | 10/2005 | Friedman et al. | |
| 7,008,401 B2 | 3/2006 | Thompson et al. | |
| 7,029,467 B2 | 4/2006 | Currier et al. | |
| 7,233,820 B2 | 6/2007 | Gilboa | |
| 7,776,005 B2 | 8/2010 | Haggstrom et al. | |
| 7,815,564 B2 | 10/2010 | Geitz et al. | |
| 7,921,848 B2 | 4/2011 | Nikolchev et al. | |
| 8,079,364 B2 | 12/2011 | Lowe et al. | |
| 8,251,975 B2 | 8/2012 | Atkins et al. | |
| 8,460,182 B2 | 6/2013 | Ouyang et al. | |
| 8,532,747 B2 | 9/2013 | Nock et al. | |
| 8,814,846 B2 | 8/2014 | Horton et al. | |
| 8,834,357 B2 | 9/2014 | Oskin et al. | |
| 8,845,522 B2 | 9/2014 | McIntyre et al. | |
| 8,961,452 B2 | 2/2015 | Purdy | |
| 9,011,412 B2 | 4/2015 | Albritto et al. | |
| 9,039,649 B2 | 5/2015 | Neisz et al. | |
| 9,370,650 B2 | 6/2016 | Hanson et al. | |
| 9,855,021 B2 | 1/2018 | Abraham | |
| 2002/0137984 A1* | 9/2002 | Chhibber | A61B 1/042 600/120 |
| 2005/0049459 A1* | 3/2005 | Hern | A61B 1/00094 600/121 |
| 2005/0096642 A1 | 5/2005 | Appling et al. | |
| 2005/0272975 A1 | 12/2005 | Mcweeney et al. | |
| 2005/0283048 A1 | 12/2005 | Gill et al. | |
| 2006/0149186 A1 | 7/2006 | Wantink et al. | |
| 2007/0118019 A1 | 5/2007 | Mitani et al. | |
| 2007/0129605 A1 | 6/2007 | Schaaf | |
| 2007/0167682 A1* | 7/2007 | Goldfarb | A61B 1/0014 600/114 |
| 2007/0197871 A1 | 8/2007 | Geitz et al. | |
| 2008/0076966 A1 | 3/2008 | Isaacson | |
| 2008/0154091 A1 | 6/2008 | Dejima et al. | |
| 2008/0167527 A1 | 7/2008 | Slenker et al. | |
| 2008/0195041 A1* | 8/2008 | Goldfarb | A61M 25/0662 604/96.01 |
| 2008/0249366 A1 | 10/2008 | Gruber et al. | |
| 2009/0054728 A1 | 2/2009 | Trusty | |
| 2009/0076498 A1 | 3/2009 | Saadat et al. | |
| 2009/0299336 A1 | 12/2009 | Jay-robinson | |
| 2010/0016757 A1 | 1/2010 | Greenburg et al. | |
| 2010/0145142 A1* | 6/2010 | Begemann | A61B 17/3421 600/104 |
| 2010/0249513 A1 | 9/2010 | Tydlaska | |
| 2010/0261967 A1 | 10/2010 | Pacey et al. | |
| 2010/0280368 A1 | 11/2010 | Can et al. | |
| 2010/0305503 A1 | 12/2010 | Fang et al. | |
| 2010/0331883 A1 | 12/2010 | Schmitz et al. | |
| 2011/0071349 A1 | 3/2011 | Drontle et al. | |
| 2011/0276113 A1 | 11/2011 | Cybulski | |
| 2011/0319718 A1 | 12/2011 | Hakanen et al. | |
| 2012/0016260 A1 | 1/2012 | To | |
| 2012/0143006 A1 | 6/2012 | Avitsian et al. | |
| 2012/0259406 A1 | 10/2012 | Schreck et al. | |
| 2012/0289858 A1 | 11/2012 | Ouyang et al. | |
| 2013/0023729 A1* | 1/2013 | Vazales | A61B 1/0669 600/104 |
| 2013/0053645 A1 | 2/2013 | Weitzner et al. | |
| 2013/0281782 A1* | 10/2013 | Zhou | A61B 1/00135 600/125 |
| 2014/0107416 A1 | 4/2014 | Birnkrant | |
| 2014/0200402 A1 | 7/2014 | Snoke et al. | |
| 2014/0357955 A1 | 12/2014 | Avitsian et al. | |
| 2014/0371737 A1* | 12/2014 | Korvick | A61B 18/1445 606/33 |
| 2015/0018622 A1* | 1/2015 | Tesar | A61B 50/13 600/202 |
| 2015/0112132 A1 | 4/2015 | Nieman et al. | |
| 2015/0202089 A1 | 7/2015 | Campbell et al. | |
| 2015/0320406 A1 | 11/2015 | Sethi | |
| 2015/0374221 A1 | 12/2015 | Sahney et al. | |
| 2016/0066770 A1 | 3/2016 | Barbato et al. | |
| 2017/0055813 A1 | 3/2017 | London brown et al. | |
| 2017/0273716 A1 | 9/2017 | Garofalo et al. | |
| 2018/0008126 A1* | 1/2018 | Arai | A61B 1/015 |
| 2018/0071481 A1 | 3/2018 | Snoke et al. | |
| 2018/0098761 A1* | 4/2018 | Stanwood | A61B 1/00128 |
| 2018/0199797 A1 | 7/2018 | London brown et al. | |
| 2019/0142400 A1 | 5/2019 | Washburn et al. | |
| 2019/0231177 A1 | 8/2019 | Dreyer et al. | |
| 2019/0374751 A1* | 12/2019 | Finson | A61M 25/0147 |

FOREIGN PATENT DOCUMENTS

| | | |
|---|---|---|
| DE | 19752430 C2 | 5/2000 |
| DE | 10045036 C1 | 7/2002 |
| WO | 2017/087579 A1 | 5/2017 |
| WO | 2019/094948 A1 | 5/2019 |

* cited by examiner

ROTATABLE INTRODUCERS

FIELD

Devices, methods, and systems of imaging and accessing various target tissue areas within a patient are provided herein.

BACKGROUND

Minimally invasive surgeries, diagnostic procedures, exploratory procedures, and other medical procedures have been favored more and more by patients and physicians given the improved healing times and the less invasive nature of the operations. Various medical devices and instrumentation have been developed to accomplish these operations, such as medical introducers, imaging devices such as fiber optic scopes, and other related endoscopic devices.

For minimally invasive surgeries to be successful, however, various target tissues and/or body cavities must be imaged and/or accessed. Accurately and efficiently imaging tissue and accessing a surgical site through a minimally invasive procedure, such as through use of a fiber optic scope, can prove challenging for a variety of reasons. For example, imaging and/or accessing tissue within a body cavity of a patient can be difficult without using introducers with larger profiles, complex guide mechanisms such as guide wires, prolonged sanitation requirements between uses, etc. However, these larger and more complex introducers can lead to greater patient discomfort and increased difficulty during and after use.

Accordingly, there remains a need for improved devices, methods, and systems of imaging and accessing target tissue sites within a patient.

SUMMARY

Devices, methods, and systems of imaging and/or accessing tissue within a patient are provided herein using various rotatable sheaths, linkages, and imaging devices. In one embodiment, an introducer system is provided that includes a rotatable sheath and a linkage. The rotatable sheath has a proximal end with a first fluid seal disposed therein, a distal end that is configured to allow imaging therethrough, and a first lumen extending between the proximal and distal ends. The rotatable sheath also has a distal portion angled at a non-zero angle relative to a longitudinal axis of a proximal portion thereof. The linkage is configured to be selectively and rotatably mated to the rotatable sheath. The linkage has proximal and distal ends with a single exit lumen on the distal end thereof and a plurality of entry lumens on the proximal end thereof such that the plurality of entry lumens merge into the exit lumen. The exit lumen is configured to align with the first lumen of the rotatable sheath and engage the first fluid seal to form a fluid seal between the rotatable sheath and the linkage when the rotatable sheath and the linkage are mated to one another. As such, fluid flow between the rotatable sheath and the linkage occurs only between the first lumen and the exit lumen.

The introducer system can have numerous variations. For example, the plurality of entry lumens can include at least a viewing entry lumen and a secondary entry lumen on the proximal end thereof. In another example, the viewing entry lumen can be configured to receive at least part of an imaging device therein and guide the imaging device into the first lumen, and the linkage can have a second fluid seal disposed therein to form a fluid seal between the imaging device and the linkage. The secondary entry lumen can also include at least one of a working lumen configured to receive surgical instruments therethrough and a fluid lumen configured to receive fluid inflow and fluid outflow therethrough. In still another example, the linkage can be configured to removably engage the rotatable sheath such that the rotatable sheath is freely rotatable about a longitudinal axis thereof independent of the linkage while preventing axial translatable between the linkage and the rotatable sheath. The linkage can also include a plurality of engagement protrusions that are configured to removably engage the rotatable sheath. In some examples, the rotatable sheath and the linkage are configured to allow passage of an imaging device, fluid, and a surgical tool through the single exit lumen of the linkage and into the first lumen of the rotatable sheath when the linkage and the rotatable sheath are mated to one another. The distal end of the linkage can be configured to engage an imaging device to prevent relative rotation or axial translation between the linkage and the imaging device. In other examples, a distal end of the first lumen of the rotatable sheath can be open such that fluid and a surgical instrument are passable therethrough.

In another aspect, an imaging system is provided that includes a rotatable sheath, a linkage, and an imaging device. The rotatable sheath has a distal end configured to allow imaging therethrough, a proximal end with a rotation hub disposed thereon, and a non-linear lumen extending between the distal and proximal ends. The linkage is configured to selectably rotatably engage the rotation hub of the sheath. The linkage has a viewing entry lumen, a secondary entry lumen, and an exit lumen, and the viewing entry lumen and the secondary entry lumen are funneled into the exit lumen. The exit lumen is configured to align with the non-linear lumen of the rotatable sheath when the sheath and the linkage are engaged. The imaging device includes a handle and an elongate imaging member that extending distally from and is formed integrally with the handle. The rotatable sheath and the linkage are configured to allow passage of the elongate imaging member and fluid through the exit lumen of the linkage and into the non-linear lumen of the rotatable sheath when the sheath and the linkage are engaged.

The imaging system can have numerous variations. For example, the rotatable sheath and the linkage can be configured to create a fluid seal therebetween when the sheath and the linkage are engaged, and the linkage and the imaging device can be configured to create a fluid seal therebetween when the linkage and the imaging device are engaged. In another example, the secondary lumen can be configured to allow passage of one of at least a surgical instrument and a fluid therethrough. In another example, the linkage can be configured to removably engage the rotation hub of the rotatable sheath to prevent axial translation between the rotatable sheath and the linkage. The linkage can also be configured to engage the handle of the imaging device to prevent relative rotation or axial translation between the linkage and the imaging device. In one example, the distal end of the rotatable sheath can be open such that fluid and a distal end of the elongate imaging member can be extendable distally therefrom. In another example, the linkage can include a plurality of engagement protrusions configured to removably engage the rotatable sheath. In still another example, the hub seal and the linkage seal can be hermetic seals.

In another aspect, a method of imaging tissue is provided that includes the step of assembling an imaging system by inserting a distal end of a linkage through a proximal end of a rotatable sheath such that a fluid seal is created between the linkage and the rotatable sheath. Assembling further includes inserting at least part of an imaging device into one of a plurality of entry lumens of the linkage, through a single exit lumen of the linkage, and into the rotatable sheath such that a fluid seal is created between the imaging device and the linkage. The linkage acts to funnel the plurality of entry lumens into the single exit lumen aligned with the rotatable sheath. After assembling the imaging system, the method includes inserting a distal end of the imaging system into a body cavity of a patient. The method further includes rotating the rotatable sheath relative to the linkage and the imaging device such that a distal end of the rotatable sheath causes a distal end of the imaging device to protrude at a plurality of non-zero angles from a longitudinal axis of a proximal portion of the rotatable sheath. The method also includes imaging tissue from the distal end of the imaging device from at least one of the plurality of non-zero angles.

The method can have numerous variations. For example, the method can also include inserting a surgical tool through a second lumen of the plurality of entry lumens such that the surgical tool is funneled from the second lumen, through the single exit lumen of the linkage, and into the rotatable sheath. The method can further include manipulating tissue disposed adjacent to a distal end of the rotatable sheath within the patient using the surgical tool protruding from the distal end of the rotatable sheath. In another example, the method can include engaging an irrigation system to a second lumen of the plurality of entry lumens such that fluid passes between the irrigation system and the body cavity of the patient through the second lumen, through the single exit lumen of the linkage, and through the rotatable sheath. In still another example, the method can include, prior to imaging tissue, extending the distal end of the imaging device from the distal end of the rotatable sheath. The method can further include withdrawing the distal end of the imaging system from the patient, and disposing of the rotatable sheath and the linkage while retaining the imaging device.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various rotatable sheaths and linkage mechanisms are provided herein for use with imaging devices to allow imaging of and access to tissue of a patient, especially tissue in a body cavity within a patient such as uterine tissue. The rotational sheaths and linkage mechanisms provided herein allow for easier use and maneuverability when imaging and accessing remote tissue within a patient while minimizing discomfort to the patient and length of the procedure. For example, the various sheaths and linkages can limit instrument profile size and maneuverability requirements to obtain various desired images and to access remote target tissue. While various medical sheaths, shafts, and/or introducers are described herein with reference to imaging devices, such as fiberscopes, that access uterine tissue, the rotational sheaths and linkages described herein can be used with a variety of types of imaging devices and can be used on a variety of target tissues or in other surgical applications.

In an exemplary embodiment, an introducer system can include a rotatable sheath and a linkage that selectively engages an imaging device. The rotatable sheath can selectively engage the linkage such that the rotatable sheath can rotate relative to the linkage and the imaging device. The rotatable sheath can also have a fluid seal disposed therein that seals around the linkage. A distal portion of the rotatable sheath can be angled so that the imaging device received in the sheath can also be angled at a variety of different angles as a result of rotation of the sheath. The linkage can have a plurality of entry lumens on its proximal end and a single exit lumen on its distal end. The linkage can thus be configured to merge the plurality of entry lumens into the exit lumen. When the sheath and the linkage are engaged, the exit lumen can be aligned with the rotatable sheath such that fluid and/or surgical instruments passed through the linkage enter the rotatable sheath. The linkage can also engage the imaging device on its proximal end to allow a portion of the imaging device to pass therethrough and into the rotatable sheath. A fluid seal can be formed between the linkage and the imaging device to protect the imaging device from fluid in the linkage and sheath. As such, a fluidly sealed passageway can be formed between an operating room environment and a body cavity of a patient when the linkage and the sheath are engaged and inserted into the patient.

FIGS. 1-9 illustrate an imaging system 10 with an angled rotatable sheath 100, a linkage 200, and an imaging device 500 assembled to one another. The angled rotatable sheath 100 is rotatable relative to the linkage 200 and the imaging device 500, and it receives a distal end 522 of the imaging device 500 therein. The rotatable sheath 100 allows imaging therethrough by the imaging device 500 with views that can be oriented in a plurality of directions as a result of rotation of the sheath 100 relative to the imaging device 500. The rotational sheath 100 has a distal end 102, a proximal end 104, a lumen 106 extending therebetween, and a longitudinal axis L1. The lumen 106 is configured to receive at least part of the imaging device 500 and various surgical instruments, fluids, suction, etc. therethrough. An angled distal tip 110 of the rotational sheath 100 is angled or curved relative to a proximal portion of the sheath 100 such that the distal tip 110 extends at a non-zero angle relative to the longitudinal axis L1. The distal end 102 thus lies offset from the longitudinal axis L1. A variety of non-zero angles can be used, such as between about 5 degrees and about 45 degrees, between about 10 degrees and about 30 degrees, about 15 degrees, etc. While the illustrated sheath 100 has the angled distal tip 110, in other embodiments the sheath 100 can be straight.

Figure 5A:
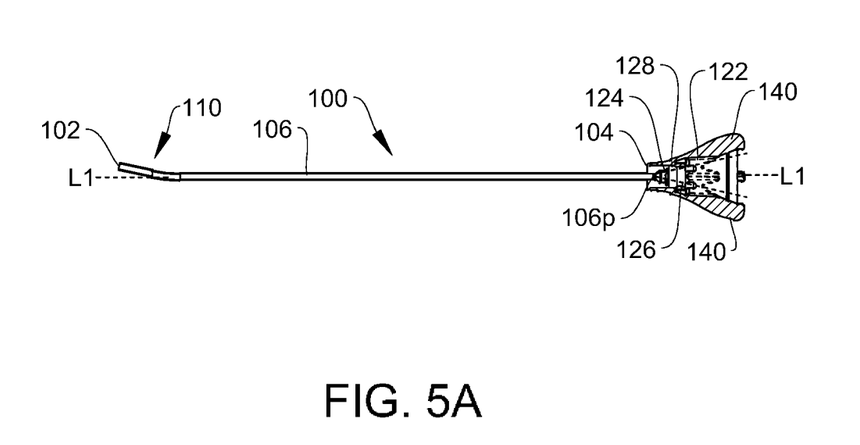
FIG. 5A is a cross-sectional side view of the rotatable sheath of the introducer system of FIG. 1.
Figure 8:
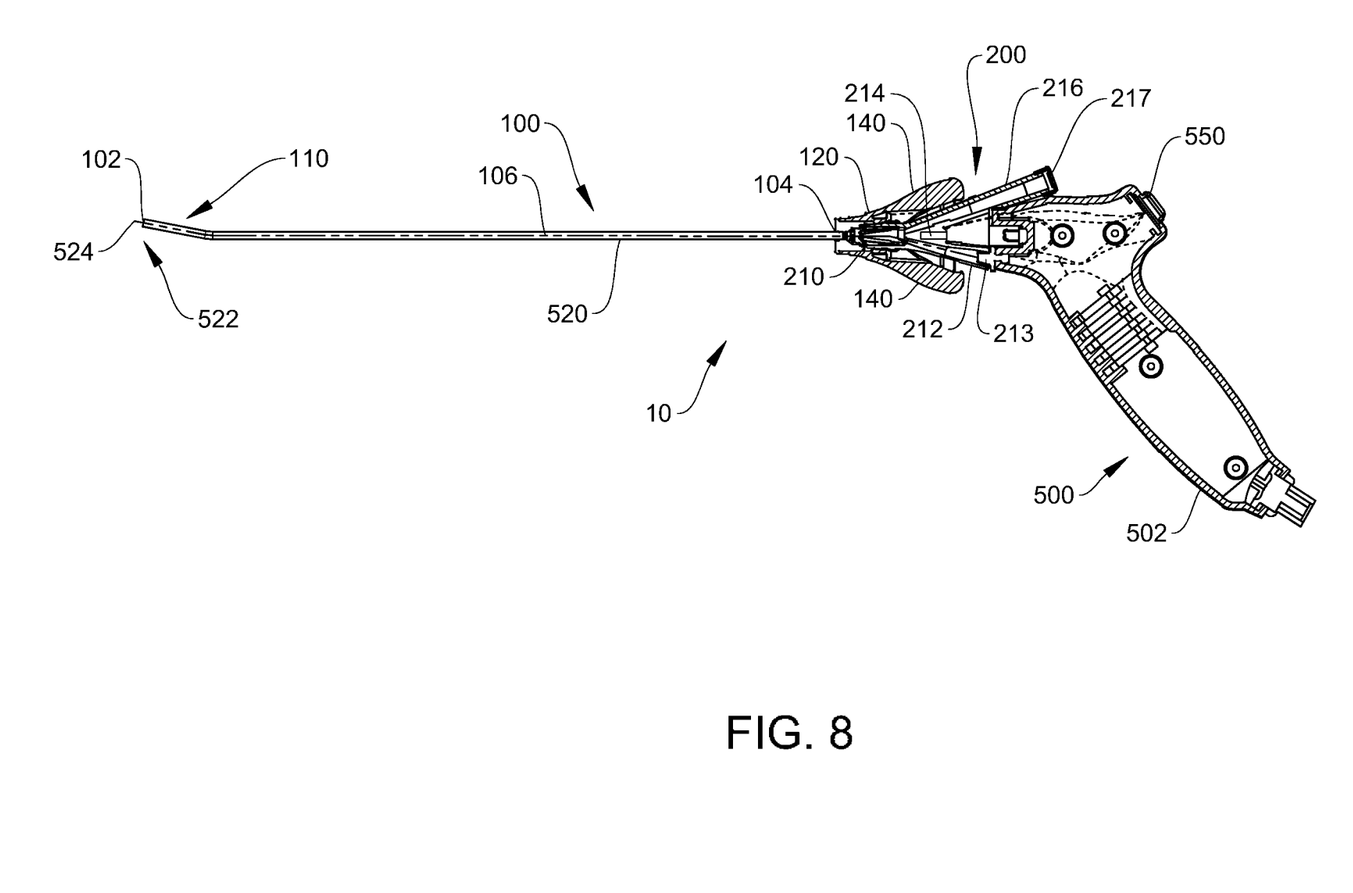
FIG. 8 is a cross-sectional side view of the introducer system and the imaging device of FIG. 1.

The distal end 102 is open to allow various surgical instruments, imaging instruments, fluids, etc. to pass through the lumen 106 and extend distally out of the opening, as shown in FIGS. 5A and 8. However, in various other embodiments, the distal end 102 can be sealed or closed, such as by an optically transparent window or lens. In some embodiments, the window can be flexible to conform to or engage in a flush manner with the distal end 522 of the imaging device 500 such that a proximal or inward-facing surface of the flexible window sits flat against the distal end 522 to eliminate air or space between the two components and allows transfer of undistorted light when the imaging device 500 obtains images therethrough, as discussed in U.S. application Ser. No. 15/885,105 to Dreyer et al. filed on Jan. 31, 2018 and incorporated herein by reference in its entirety. The illustrated sheath 100 is disposable after each use. However, in some embodiments, the sheath 100 can be designed for reuse, such as through sterilization. The sheath 100 can be made out of various materials, such as plastic, metal, semi-rigid materials such as thermoplastic elastomers, silicone, etc. In some embodiments, materials such as optically clear plastics can be used to allow imaging directly therethrough at one or more sections thereof. The sheath 100 can be manufactured in a variety of ways, such as through injection molding, machining, casting, 3D printing, etc.

Figure 5B:
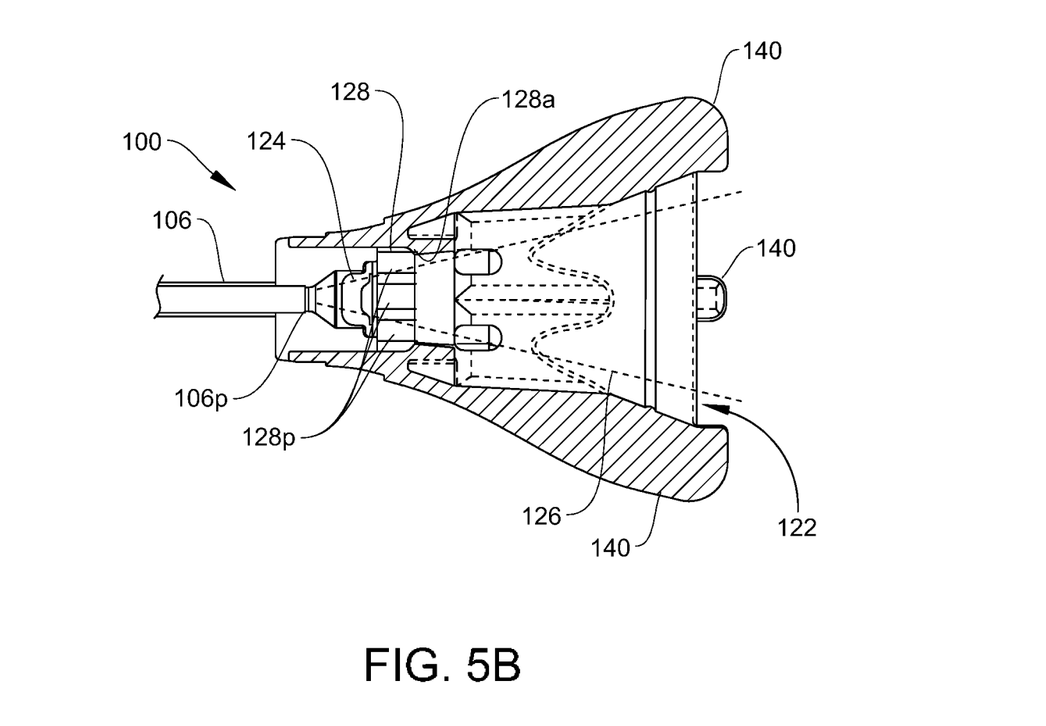
FIG. 5B is a cross-sectional side view of a proximal portion of the rotatable sheath of the introducer system of FIG. 1.
Figure 7A:
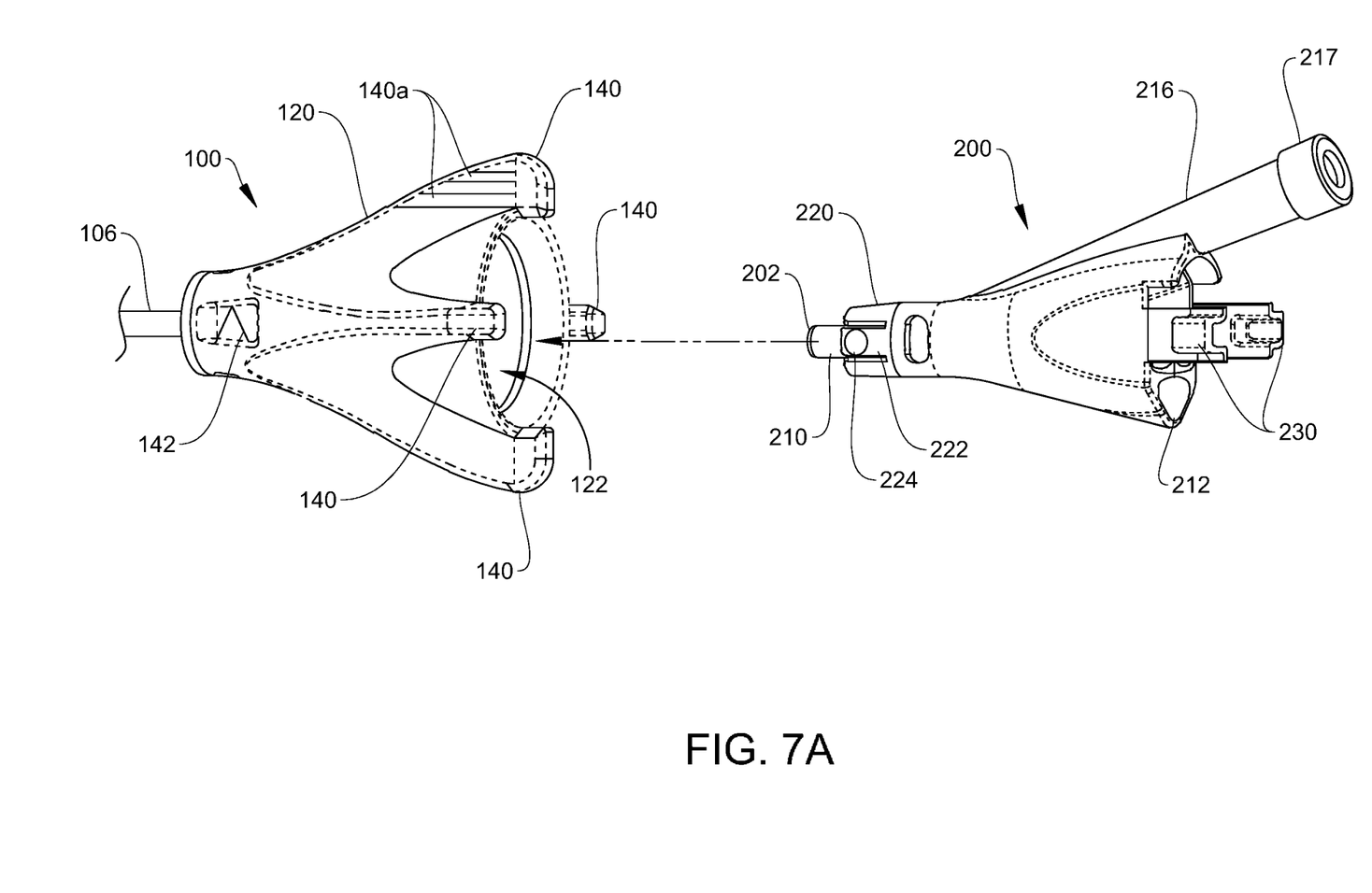
FIG. 7A is a perspective view of the linkage being inserted into the rotatable sheath of the introducer system of FIG. 1.
Figure 7B:
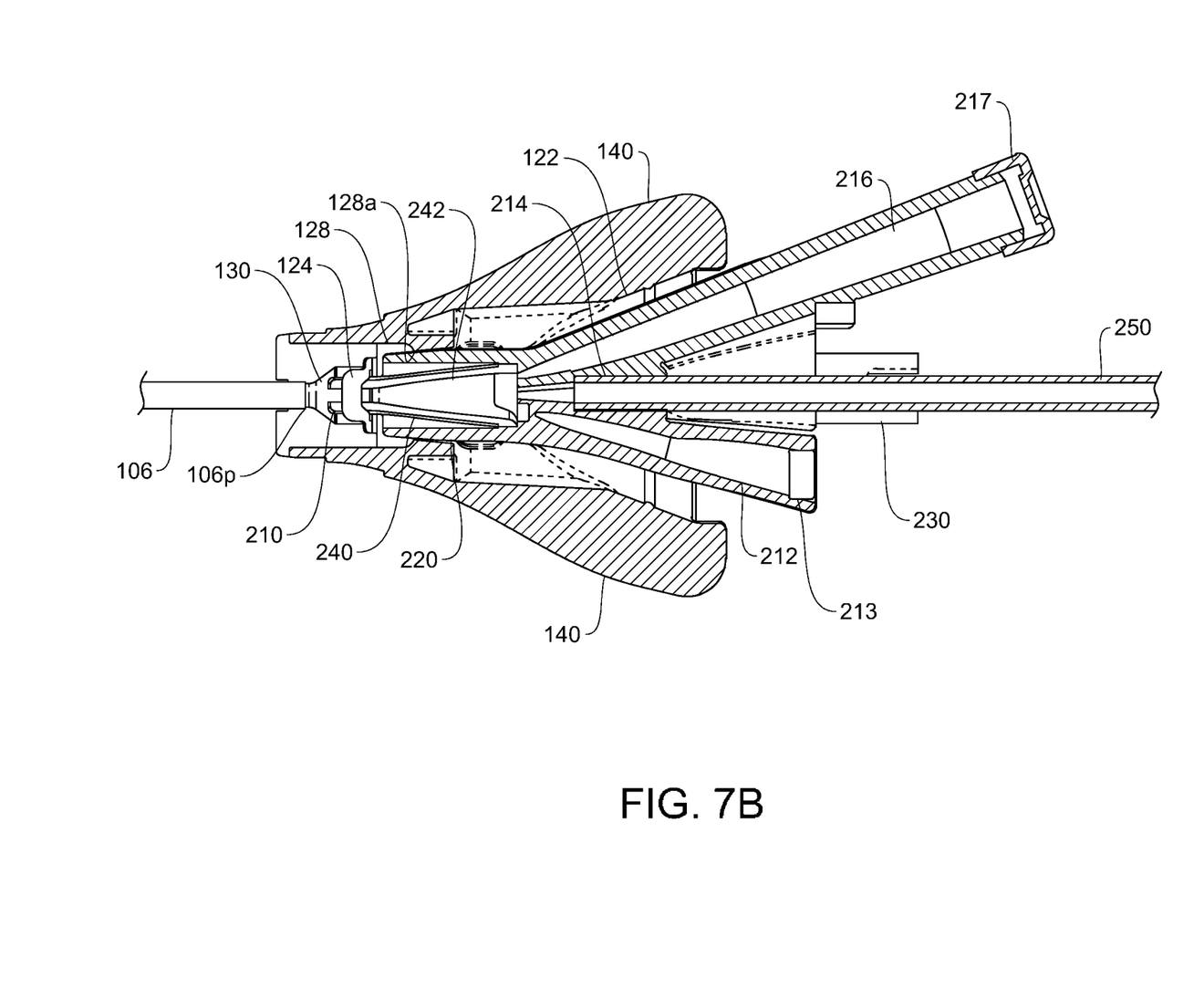
FIG. 7B is a cross-sectional side view of the linkage engaged with the rotatable sheath of the introducer system of FIG. 1.

The proximal end 104 of the rotatable sheath 100 includes a rotation hub 120 that is configured to rotatably engage the linkage 200, as shown in FIGS. 5B, 7A, and 7B. As such, the rotatable sheath 100 is selectively rotatable independent of the linkage 200 while proximal or distal translation along the axis L1 is prevented. While such a connection can be made in a variety of ways, in one embodiment, the rotation hub 120 has a receiving cavity 122 on a proximal-facing surface thereof that receives part of the linkage 200 therein, a rotatable seal 124, and a channel 126 that leads from the receiving cavity 122 into the lumen 106.

Figure 5C:
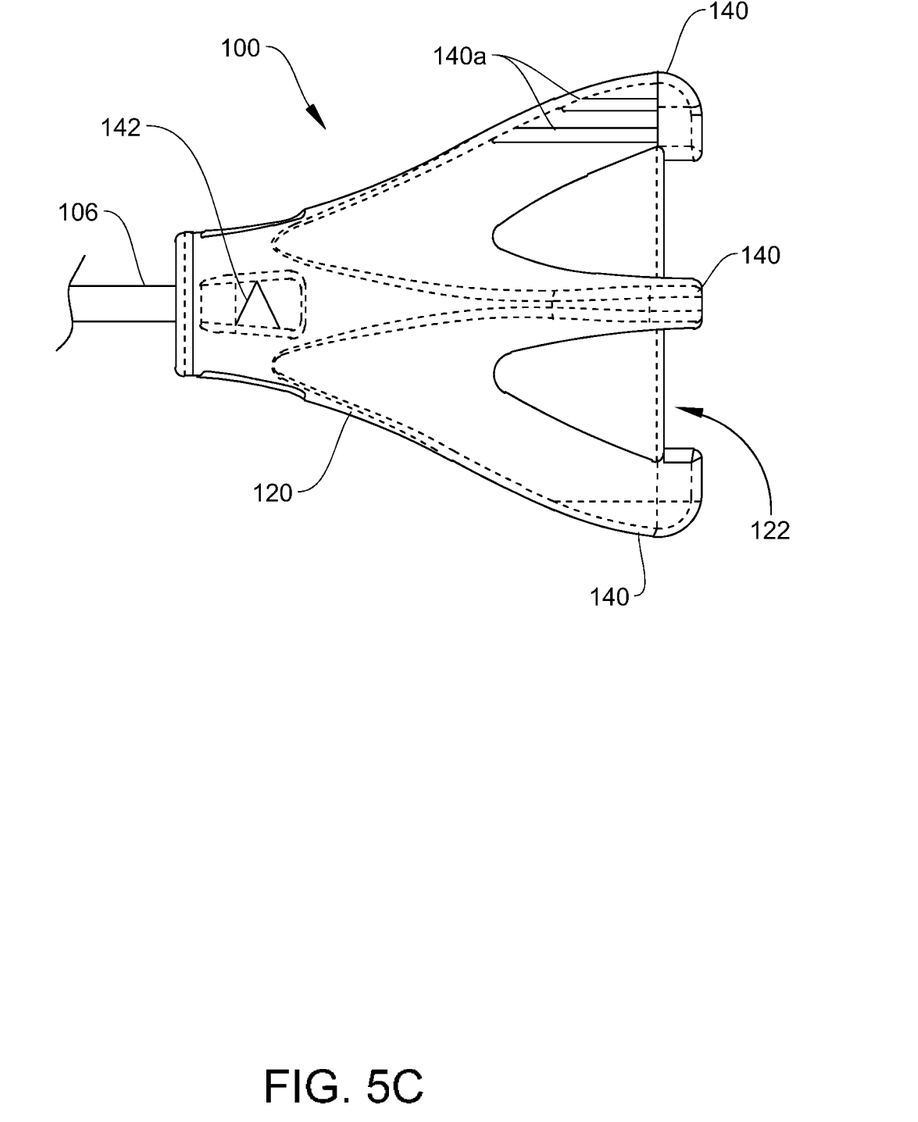
FIG. 5C is a side view of a proximal portion of the rotatable sheath of the introducer system of FIG. 1.

As shown in FIGS. 5A-5C, the receiving cavity 122 has a generally conical or tapered shape leading to the proximal open end of the lumen 106 to assist a user in inserting a distal end 202 of the linkage 200 therein and to assist in the passage of instruments, fluid, etc. during use. The receiving cavity 122 receives a cylindrical distal portion 220 of the linkage 200 upon insertion of the linkage 200 therein. As illustrated in FIG. 5A, a cylindrical groove 128 is formed in the cavity 122 to engage a plurality of protrusions 224 extending radially outward from a plurality of flexible tabs 222 that are formed from the cylindrical distal portion 220 of the linkage 200. As illustrated in FIGS. 5B and 7B, a lip 128a of the groove 128 contacts and forces the protrusions 224 radially inward during insertion of the linkage 200 into the cavity 120, which causes the flexible tabs 222 to bend radially inward to allow the protrusions 224 to pass distally across the lip 128a and into the groove 128. When the linkage 200 is fully inserted, the groove 128 allows the protrusions 224 to return radially outward to engage the groove 128 as the tabs 222 return to their resting state. Thus, the rotatable sheath 100 can rotate in a full 360-degree circle about the axis L1 relative to the linkage 200 as the cylindrical groove 128 rotates around the protrusions 224. However, the groove 128 still engages the protrusions 224 to prevent proximal or distal translation of the rotatable sheath 100 once it has engaged the linkage 200. As such, the distal tip 110 of the rotatable sheath 100 can rotate in full 360-degree circles and be oriented in a plurality of different directions relative to the linkage 200 and the imaging device 500 as a result of rotation of the sheath 100 and the non-zero angle of the distal tip 110. In some embodiments, the groove 128 can have one or more detents formed therein. For example, a plurality of detents 128b are formed on the groove 128 to receive the protrusions 224 and hold the rotatable sheath 100 at selectable rotational positions relative to the linkage 200, as illustrated in FIG. 5B. This engagement maintains an orientation of the distal tip 110 in a selected direction without having to exert a manual force to maintain a position. In some embodiments, the detents can be formed at pre-set intervals, such as every 15 degrees, every 30 degrees, every 45 degrees, every 60 degrees, every 90 degrees, etc. about the cylindrical surface of the groove 128 to allow a user to rotate the distal tip 110 to common or pre-determined angles during use.

The rotation hub 120 also has rotatable seal 124 disposed therein for sealing around the linkage 200 upon insertion of the linkage 200 therein and for maintaining a seal during rotation of the sheath 100, as shown in FIGS. 5B and 7B. The seal 124 allows a distal end 202 of the linkage 200 to pass distally therethrough to allow fluid flow and instrument access between the distal end 202 of the linkage 200 and the lumen 106 of the sheath 100. The seal 124 forms around an outer radial surface of the distal end 202 of the linkage 200 such that the seal is maintained even when the seal 124 is rotated as a result of rotation of the sheath 100 relative to the linkage 200. As such, fluid flow between internal portions of the rotatable sheath 100 and the linkage 200 occur only between a proximal end 106p of the lumen 106 and the distal end 202 of the linkage 200. The seal 124 is formed in a smaller transition cavity 130 at the distal-most end of the receiving cavity 122 and into which the distal end 202 of the linkage 200 terminates and the lumen 106 of the sheath 100 opens. The transition cavity 130 has a tapered or conical shape to assist when passing instruments, fluid, etc. into the lumen 106. The cavities 122, 130 thus define the channel 126 that leads from the receiving cavity 122 into the lumen 106 to guide insertion of the linkage 200 through the seal 124 and allow instrument and fluid passage between the linkage 200 and the lumen 106 of the sheath 100. In some examples, the seal 124 can be a hermetic seal. In various embodiments, the seal 124 can either be formed integral with or be a separate component from and insertable into the hub 120. The seal 124 can be made from a variety of materials, such as silicone, thermoplastic elastomers, etc. In some embodiments, the seal can be formed by placing a gasket such as an O-ring within an inner radial surface of the cavity 122 and/or around the outer radial surface of the distal end 202 of the linkage 200. Additionally and/or alternatively, in some embodiments, a sealing mechanism can be placed within a proximal portion of the lumen 106 itself either to assist the seal 124 or instead of the seal 124.

Figure 1:
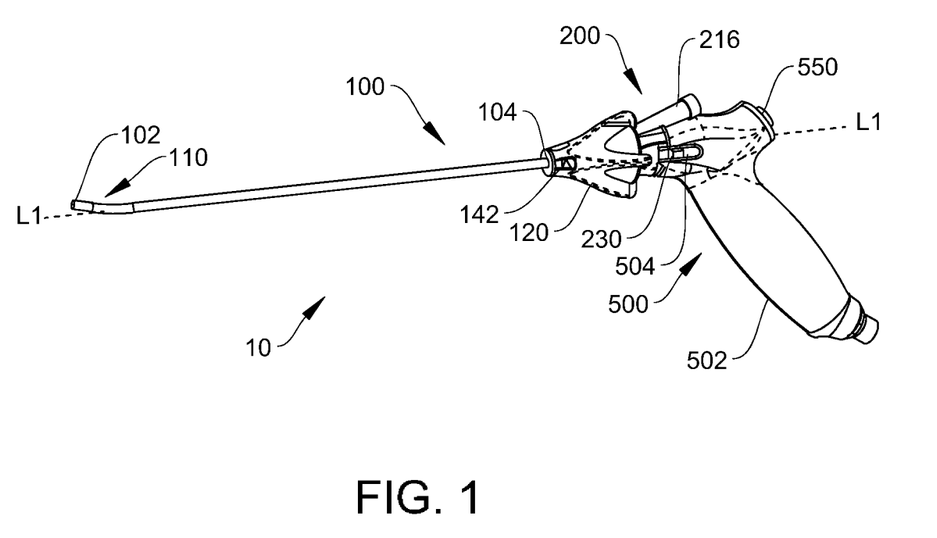
FIG. 1 is a perspective view of one embodiment of an introducer system with an imaging device.
Figure 2:
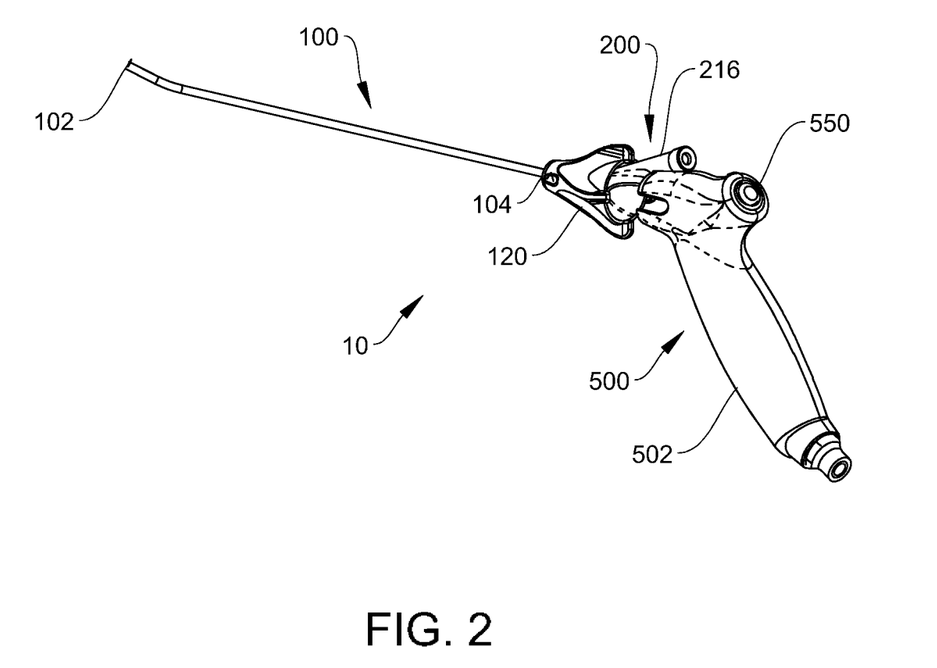
FIG. 2 is a perspective view of the introducer system and the imaging device of FIG. 1.
Figure 3:
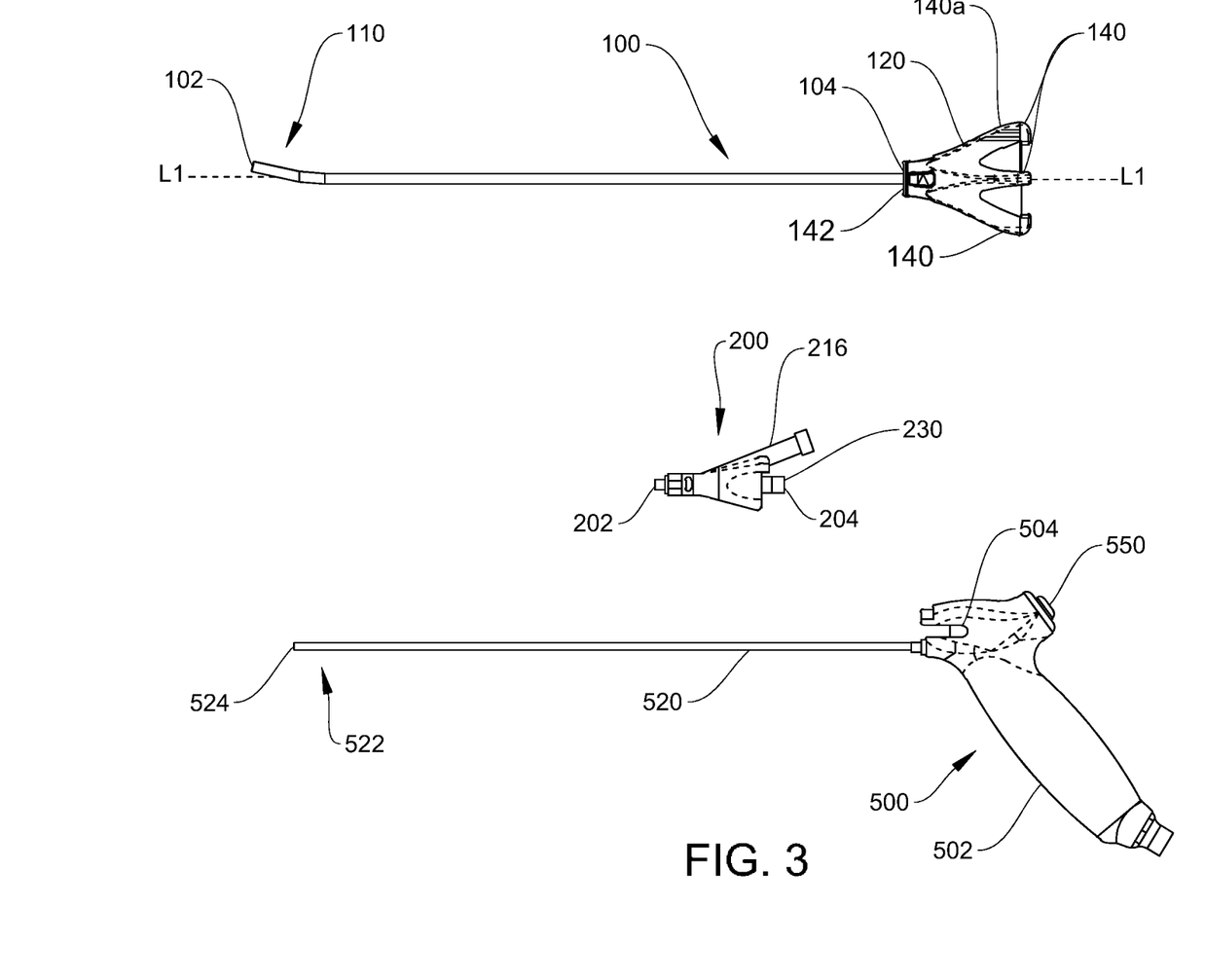
FIG. 3 is a side view of the introducer system and the imaging system of FIG. 1 disassembled.
Figure 4:
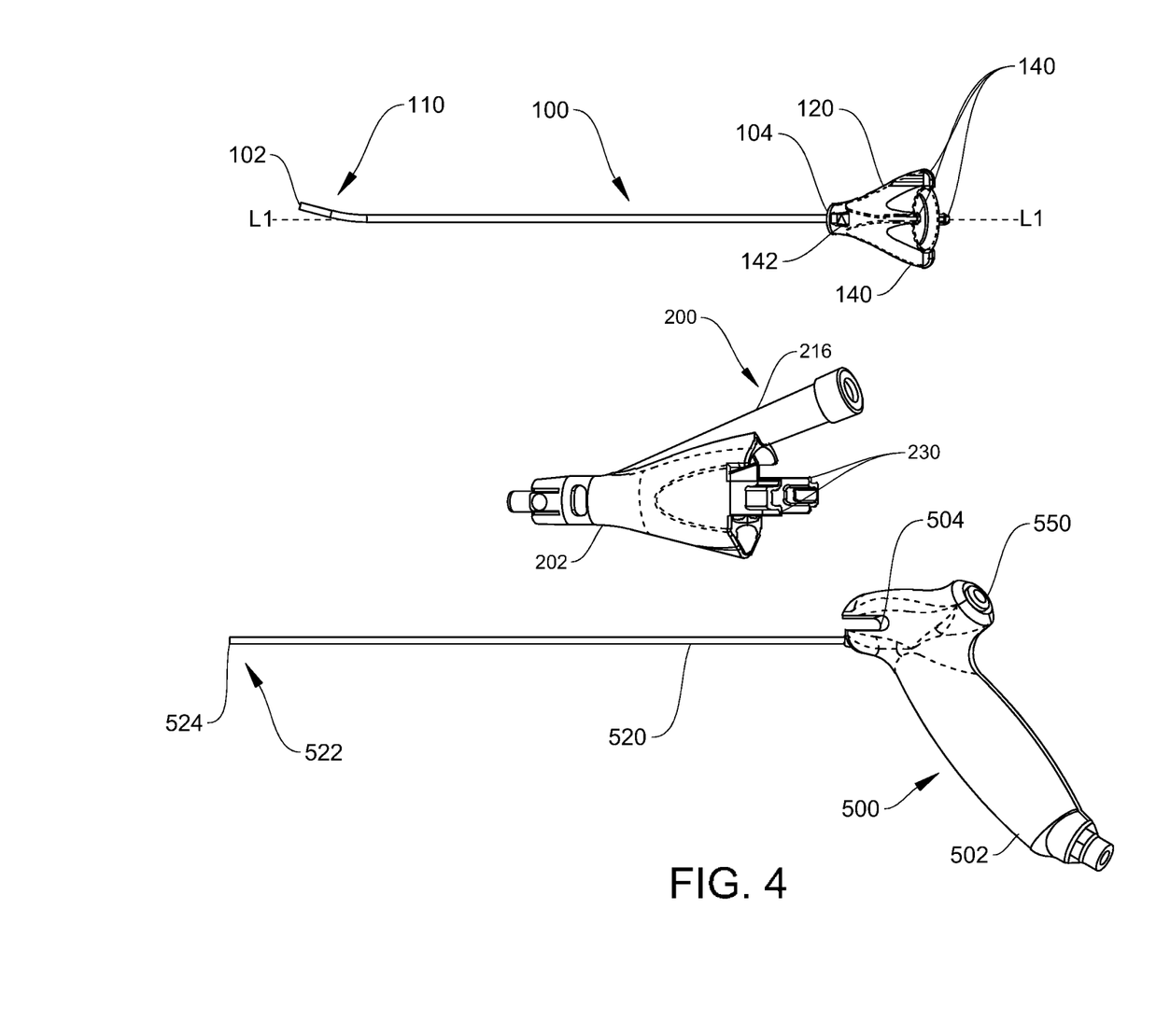
FIG. 4 is a perspective view of the introducer system and the imaging system of FIG. 1 disassembled.

The rotation hub 120 also has one or more gripping elements 140 thereon to assist a user in gripping and rotating the rotatable sheath 100. The illustrated gripping elements 140 are wings extending radially outward therefrom, however a variety of different elements can be used, such as textured surfaces, protrusions, ribs, handles, etc. The hub 120 can also have one or more directional indicators on an external surface thereof to indicate to a user the orientation of the angled distal tip 110 relative to the surrounding environment during use of the device. For example, an indicator 142 in the form of an arrow or triangle is illustrated in FIGS. 1, 3, and 4 that is oriented in the direction of the curve of the angled distal tip 110 and the distal end 102. In other embodiments, various alternative indicators can also be used, such as lines, protrusions, labeling, etc., and various indicators 142 can be placed at various points around the hub 120, such as every 90 degrees. The gripping elements 140 can be used as directional indicators in some embodiments. For example, a visually distinct wing can be oriented in a same direction as the curve of the angled distal tip 110, such as ribs 140a formed one of the gripping element 140 illustrated in FIG. 3.

As mentioned above, the linkage 200 is rotatably engageable with the rotatable sheath 100 on its distal end 202, and it is engageable with the imaging device 500 on a proximal end 204 thereof. The linkage 200 has a plurality of entry lumens on a proximal portion thereof and a single exit lumen 210 on the distal end 202 thereof, and it is configured to merge the entry lumens into the exit lumen 210 therewithin, as illustrated by the arrows in FIGS. 6B and 7B. For example, the illustrated linkage 200 has a viewing lumen 212, a fluid lumen 214, and a working lumen 216. However, in other embodiments, fewer or more entry lumens can be provided for a variety of different purposes, such as distinct fluid inflow and fluid outflow lumens, one or more additional working lumens, etc. The illustrated linkage 200 is disposable after each use. However, in some embodiments, the linkage 200 can be designed for reuse, such as through sterilization. The linkage 200 can be made out of various materials, such as plastic, metal, semi-rigid materials such as thermoplastic elastomers, silicone, etc. The linkage 200 can be manufactured in a variety of ways, such as through injection molding, machining, casting, 3D printing, etc.

The exit lumen 210 of the linkage 200 protrudes distally from the linkage 200 to guide passage of fluid and/or instruments from within the linkage 200 and into the rotatable sheath 100. The exit lumen 210, which has an approximately cylindrical shape, is insertable along the channel 126 on the rotation hub 120 as illustrated by the arrow in FIG. 7A, through the receiving cavity 122, and through the seal 124 to be aligned with the proximal open end 106p of the lumen 106 in the rotatable sheath 100 as illustrated in FIG. 7B. The exit lumen 210 terminates proximal to the proximal open end 106p of the lumen 106 in the transition cavity 130 of the hub. As such, instruments, fluid, etc. that pass through the exit lumen 210 will pass through the transition cavity 130 before entering the lumen 106. However, in other embodiments, the exit lumen 210 can be configured to enter into and/or seal directly to the open proximal end 106p of the lumen 106. Additionally, while the lumen 210 is illustrated with a cylindrical shape and an approximately circular cross-section, a variety of different shapes can be used in different embodiments, such as oval, octagonal, etc. The outer radial surface of the exit lumen 210 receives the seal 124 therearound such that the seal is maintained upon insertion of the exit lumen 210 and rotation of the rotatable sheath 100. In some embodiments, a gasket such as an O-ring or another sealing mechanism can be placed around the outer surface of the exit lumen 210 to create the seal between the rotatable sheath 100 and the linkage 200. In other embodiments, a sealing mechanism can be placed within the exit lumen 210 itself either to assist the seal 124 in the rotation hub 120 or instead of the seal 124.

Figure 6A:
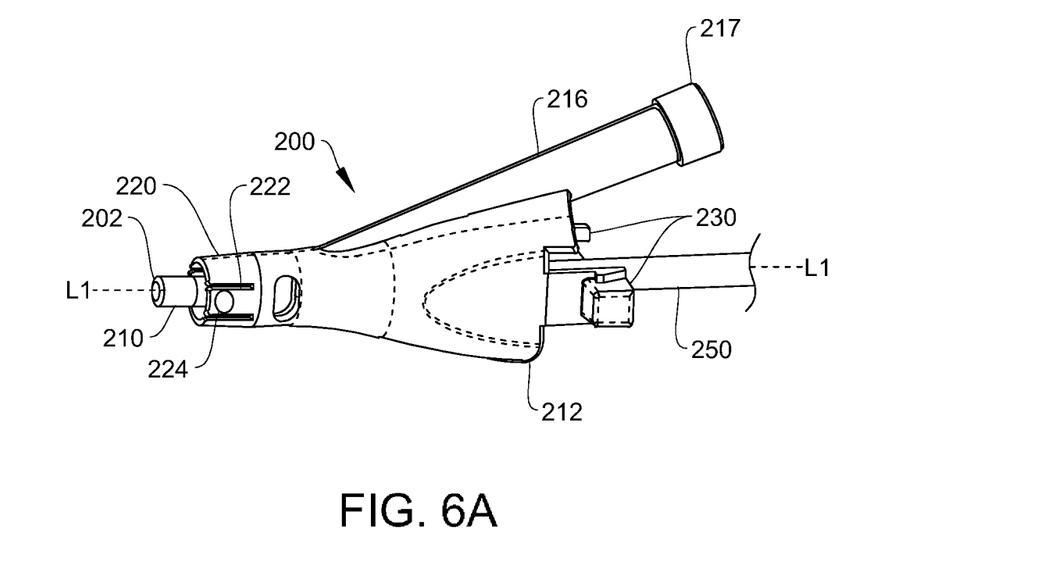
FIG. 6A is a side view of the linkage of the introducer system of FIG. 1.
Figure 6B:
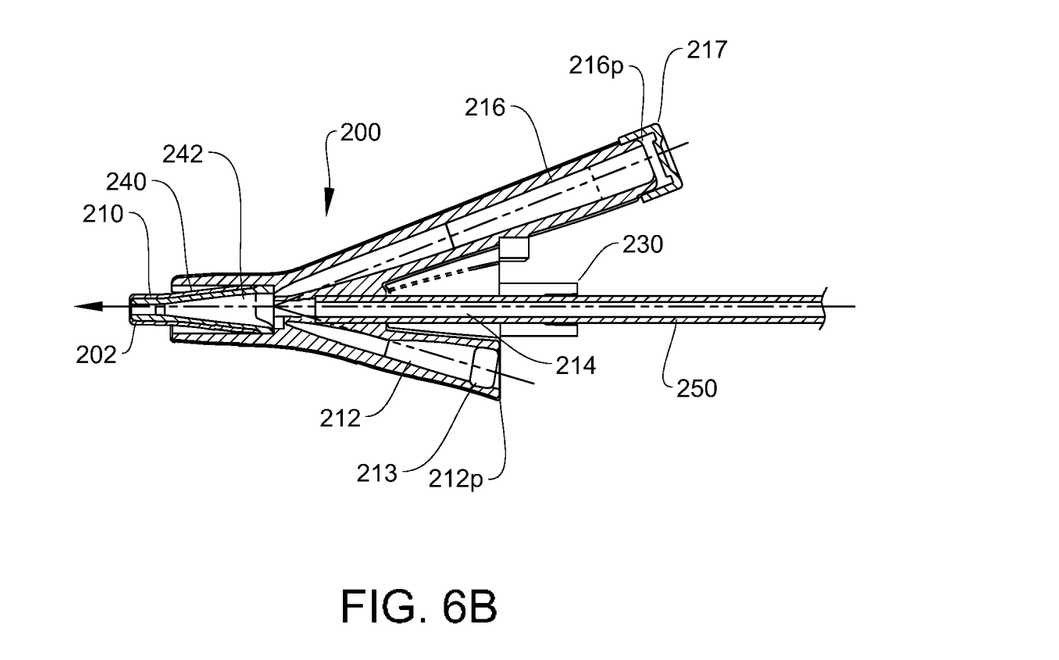
FIG. 6B is a cross-sectional side view of the linkage of the introducer system of FIG. 1.

A funnel element 240 defines an inner cavity 242 within the linkage 200 and leads distally to the exit lumen 210, as illustrated in FIG. 6B. The funnel element 240 has a funnel shape with a wider end of the cavity 242 on a proximal side of the linkage 200 so as to be configured to receive the plurality of entry lumens. The funnel element 240 also has a narrower end on a distal side of the linkage 200 to merge or funnel any instruments, fluids, etc. passed through the entry lumens into the exit lumen 210, as illustrated by the lines and arrow in FIG. 6. The illustrated cavity 242 has a generally conical shape with a circular proximal opening and a taper to the exit lumen 210. However, in other embodiments, the funnel element 240 and the inner cavity 242 can have various different shapes, such as pyramidal, etc. based on desired use.

The cylindrical distal portion 220 of the linkage 200, discussed above, extends radially around the funnel element 240 and protrudes distally parallel to the axis L1 to engage the rotatable sheath 100, as illustrated in FIG. 6A. As mentioned above, a plurality of semi-spherical protrusions 224 extends radially outward from a plurality of flexible tabs 222 formed from the cylindrical distal portion 220, and they flex radially inward to pass distally by the lip 128a of the groove 128 and return radially outward to engage the groove 128. While the distal portion 220 with the flexible tabs 222 and protrusions 224 is illustrated herein, in other embodiments, different engagement means can be used to allow the sheath 100 and the linkage 200 to rotatably engage each other, such as protruding fingers, magnetic engagements, various spring-biased engagements, etc.

Figure 9:
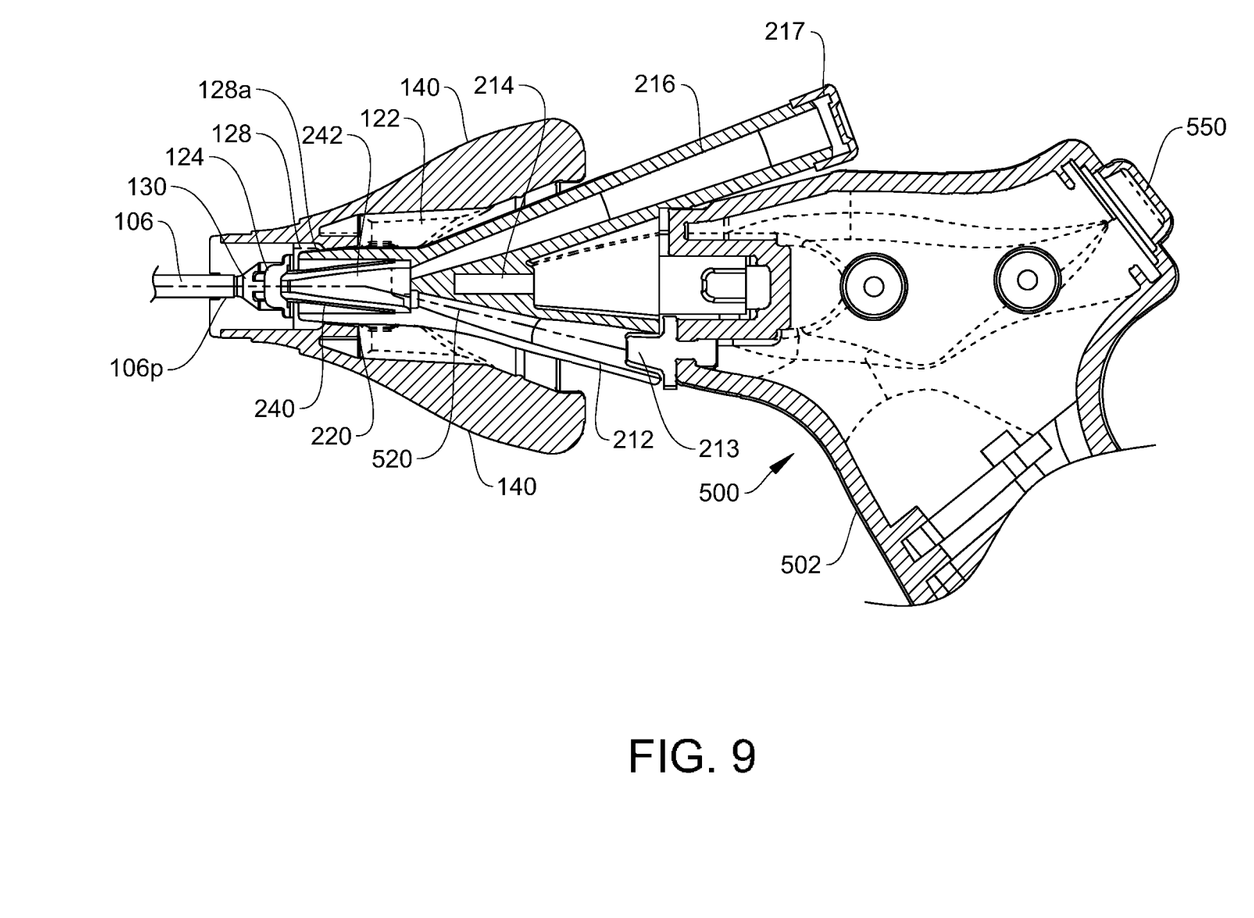
FIG. 9 is a cross-sectional side view of a proximal portion of the introducer system and the imaging device of FIG. 1.

The various entry lumens extend proximally from the funnel element 240. The illustrated linkage 200 has a viewing lumen 212, a fluid lumen 214, and a working lumen 216, as shown in FIGS. 6A, 6B, 7B, 8, and 9. However, as noted above, a variety of different lumens can be used. The viewing lumen 212 can receive various imaging devices therein to access, for example, a body cavity of a patient for imaging. The lumen 212 has an opening on its proximal end 212p that is configured to receive the imaging device 500. As such, the viewing lumen 212 guides the elongate imaging member 520 into the funnel element 240, from which it can pass through the exit lumen 210, enter the lumen 106, and optionally extend from the distal end 102 thereof, as shown in FIGS. 8 and 9. A seal 213 is formed in a proximal portion of the viewing lumen 212 that accepts the elongate imaging member 520 of the imaging device 500 and seals around the imaging member 520. As such, any fluid in the linkage 200 and/or the sheath 100 is prevented from passing proximally through the seal 213 and coming into contact with a proximal portion of the imaging device 500. This ability to prevent fluid contact can eliminate or minimize the need to sterilize the imaging device 500 after use. While the illustrated sheath 100 is open on its distal end 102 and thus fluid can enter the viewing lumen 212 when the sheath 100 is inserted into a patient, in some embodiments in which the distal end 102 of the sheath 100 is sealed, the viewing lumen 212 can be sealed from fluid contact. As such, when the elongate imaging member 520 is inserted therein, it will not contact fluid. In various other embodiments, the seal 213 can be formed on the imaging device 500 and/or can be positioned between the viewing lumen 212 and the imaging device 500. As such, it can be formed integral with or be separate from and insertable into the viewing lumen 212 and/or the imaging device 500. In some embodiments, the seal 213 can be disposable and replaceable separate from the imaging device 500 and/or the linkage 200. The seal 213 can take various forms, such as a compression silicone seal, an o-ring style seal, etc. The seal 213 can be a hermetic seal, and it can be made from a variety of materials, such as silicone, thermoplastic elastomers, etc.

The linkage 200 also has a fluid lumen 214 as shown in FIGS. 6B and 7B, which is configured to engage various irrigation tubes to allow fluid inflow and fluid outflow to or from a body cavity of a patient. The lumen 214 has an opening on its proximal end 214p that is configured to engage with an irrigation tube 250. One or more seals, engagements, mechanisms, valves, etc. can be disposed on its proximal ends 214p to allow engagement with the tube 250, as explained further in U.S. Patent App. Pub. No. 2017/0055813 to London Brown, et al. filed on Oct. 5, 2016 and incorporated herein by reference in its entirety.

The linkage 200 furthermore has a working lumen 216, for example illustrated in FIGS. 6A and 6B, that is configured to receive various surgical instruments therein to access the body cavity of the patient therethrough. The lumen 216 has an opening on its proximal end 216p that is configured to receive various surgical tools therethrough, such as forceps, biopsy tools, graspers, etc. As such, the working lumen 216 guides surgical tools into the funnel element 240, from which they can pass through the exit lumen 210, enter the lumen 106, and extend distally from the distal end 102 thereof. The illustrated proximal end 216p has an engagement mechanism 217 configured to engage, secure, and/or form a seal around a surgical instrument inserted into the working lumen 216. Similar to the fluid lumen 214, various engagement mechanisms can be used in various embodiments, such as luer fits, fluid seals, O-ring seals, hermetic seals, valves, etc., as explained further in U.S. Patent App. Pub. No. 2017/0055813 to London Brown, et al. incorporated above.

The linkage 200 also has an engagement mechanism 230 that is configured to engage the imaging device 500 on a proximal end of the linkage 200, as illustrated in FIGS. 1-4. The engagement mechanism 230 releasably secures the imaging device 500 with respect to the linkage 200 such that the imaging device 500 and the linkage 200 effectively operate as a single component when engaged, preventing any relative rotation and/or axial translation therebetween. For example, the engagement mechanism 230 can include one or more engagement fingers configured to engage corresponding features on the imaging device 500, such as in snap or friction fit engagements. The fingers can be configured to be engaged or disengaged by a user, such that the linkage 200 is removably, non-rotatably, and non-slidably affixed to the imaging device 500 in use. Additionally, a variety of engagement features can be used, such as seals, clips, posts, locks, etc.

As discussed above, the imaging device 500 is configured to engage the linkage 200 and extend into the rotatable sheath 100, as shown in FIGS. 1-4, 8, and 9. The imaging device 500 has a handle 502 and an elongate imaging member 520 extending distally from and formed integrally with the handle 502. The elongate imaging member 520 extends from the handle 502 and is flexible such that it can be inserted into the viewing lumen 212, through the linkage 200 to pass through the exit lumen 210, and into the lumen 106 of the rotatable sheath 100. The imaging member 520 can obtain images, such as images of the body cavity in the patient, various images of tissue samples, images of placement and/or positioning of the sheath 100 and/or surgical tools used with the sheath 100, etc. The elongate imaging member 520 extends through the sheath 100 and terminates protruding distally from the distal end 102 of the sheath 100 when the sheath 100, the linkage 200, and the imaging device 500 are assembled. However, in other embodiments, the elongate imaging member 520 can terminate proximal to the distal end 102 of the sheath 100 at a point within the sheath 100 or it can terminate at the distal end 102, for example when a flexible window is used to seal the distal end 102 of the sheath 100 and to conform to the distal end 522 of the imaging device as discussed above. The elongate imaging member 520 has an imaging unit 524 engaged on the distal end 522 thereof for use with imaging. The imaging unit 524 can take a variety of forms, such as an active pixel sensor array or a Complementary Metal-Oxide Semiconductor (CMOS) sensor as provided in more detail in U.S. Patent App. Pub. No. 2017/0055813 to London Brown, et al. incorporated above. The imaging unit 524 can communicate with the handle 502 and/or various imaging systems, servers, etc. and can be configured to take images of areas adjacent thereto with assistance from various light transmission devices. The light transmission devices can include fiber optic elements or light delivery fibers, and can be flexible to allow for bending and flexing within the linkage 200 and the sheath 100.

A receiving engagement 504 on the handle 502 is configured to engage with the engagement mechanism 230 of the linkage 200 such that the handle 502 and the linkage 200 do not rotate or axially translate relative to each other during use, as noted above. As such, the elongate imaging member 520 is non-slidable relative to and non-rotatable about the longitudinal axis L1 when the imaging device, the linkage 200, and the rotatable sheath 100 are engaged. However, a distal portion of the elongate imaging member 520 that includes the distal end 522 and the imaging unit 524 is angled away from the axis L1 by the angled distal tip 110 of the sheath 100. Because the imaging member 520 is flexible, it bends at the same non-zero angle as the angled distal tip 110 when inserted therethrough, and the imaging unit 524 obtains images while being oriented away from the axis L1 at the non-zero angle. As the rotatable sheath 100 is rotated about the axis L1 during use, the elongate imaging member 520 can thus obtain images from a variety of different orientations about the axis L1 by being bent or angled in different directions while not actually being rotated. This ensures the elongate imaging member 520 is not twisted or damaged during use, allowing use of the imaging device 500 that can take high quality images therefrom while not being damaged during use and still allowing a user to obtain images from a variety of different angles with minimal discomfort to a patient.

The handle 502 can have a pistol grip to assist the user in maneuvering the imaging device 500, however a variety of different handle shapes can be used, such as a pencil grip. In some embodiments, the handle 502 can include a light source disposed within the handle 502. The imaging device 500 can also be configured to connect to a power source. For example, a power source can be disposed in the handle 502, or the power source can be external to the device 500 and selectively connect to the handle 502. A communication element 550 can also be operably engaged with the handle 502 such that the communication element 550 is in signal communication with the imaging unit 524 and configured to receive an image signal therefrom associated with an image captured by the imaging unit 524. In addition, a display device for displaying the image, and/or various computer devices for storing or analyzing the image, can be in communication with the communication element 550 via a wired or wireless connection. All connections provided herein can thus be either wired or wireless connections.

In use, a user joins the linkage 200 to the rotatable sheath 100. For example, the user inserts the distal end 202 of the linkage 200 into the receiving cavity 122 of the rotation hub 120, as illustrated by an arrow in FIG. 7A. The user continues insertion until the protrusions 224 of the cylindrical distal portion 220 of the linkage 200 engage the groove 128 of the cavity 122 and the exit lumen 210 passes through the seal 124 to align with the lumen 106. The user also joins the imaging device 500 to the linkage 200, as illustrated in FIGS. 8 and 9. For example, the user inserts the elongate imaging member 520 through the viewing lumen 212 and the seal 213, along the cavity 242, through the exit lumen 210, and through the lumen 106 of the rotatable sheath 100 until the receiving engagement 504 on the handle 502 engages with the engagement mechanism 230 of the linkage 200. The user can optionally attach the irrigation tube 250 to the fluid lumen 214. During a surgical procedure, the user inserts the distal end 102 of the sheath 100 into a body cavity of a patient, such as a uterus. As such, the user can create a sealed passageway from an exterior of the patient into the body cavity of the patient. The user can optionally use images obtained by the imaging device 500 to assist in navigation, positioning, and/or placement of the distal end 102 adjacent to target tissue. The user can rotate the rotatable sheath 100 relative to the linkage 200 and the imaging device 500 during insertion and/or after placement to assist in navigation, to obtain desired images of adjacent tissue such as uterine tissue or a surgical site, to provide easier access to target tissue such as uterine tissue for a surgical instrument, etc. The user can provide irrigation and/or create suction through the fluid lumen 214 by actuating various irrigation systems connected to the irrigation tube 250. The user can also pass various surgical instruments or tools through the working lumen 216 as needed to access and manipulate target tissue. Thus, the user can rotate the rotatable sheath 100 to allow more desirable images to be taken and to provide easier access to various surgical sites during use while minimizing repeated insertions and extractions and minimizing a profile of the insertable portion of the imaging system 10 to increase patient comfort and ease of use. When the procedure is completed and a user has obtained any desired images and performed any desired tissue manipulation, the user removes the sheath 100 from the body cavity, optionally using images obtained from the imaging device 500 to guide removal as needed.

The various sheaths, linkages, imaging devices, etc. disclosed herein can be provided in any of a variety of sizes, depending on patient anatomy, procedure type, imaging device to be used, and various other parameters which will be readily apparent to one having ordinary skill in the art. In some embodiments, the sheaths disclosed herein can have a variety of lengths, for example, about 10 cm to 40 cm, and can have a variety of diameters, such as about 1 mm to 6 mm.

In the present disclosure, like-numbered components of the embodiments generally have similar features, and thus within a particular embodiment, each feature of each like-numbered component is not necessarily fully elaborated upon. The figures provided herein are not necessarily to scale. Although the devices and methods disclosed herein are generally directed to surgical techniques, they can also be used in applications outside of the surgical field.

Although the invention has been described by reference to specific embodiments, it should be understood that numerous changes may be made within the spirit and scope of the inventive concepts described. Various features of the imaging and/or introduction system and methods of the present invention may be accomplished singularly, or in combination, in one or more of the embodiments of the present invention. Although particular embodiments have been described, it should be recognized that these embodiments are merely illustrative of the principles of the present invention. For example, in all cases, any of the features that are disclosed herein can be combined with any of the other features that are disclosed (even if those two or more distinct features appear in different sections of the above-written description and/or are associated with different embodiments). Accordingly, it is intended that the invention not be limited to the described embodiments, but that it have the full scope defined by the language of the following claims.

What is claimed is:

1. An imaging system, comprising:
    a sheath having a distal end configured to allow imaging therethrough, a proximal end, and only a single lumen extending between the distal and proximal ends, the sheath having an angled distal portion that is angled at a fixed non-zero angle relative to a straight proximal portion of the sheath, the straight proximal portion extending along a longitudinal axis of the sheath, the sheath having a plurality of gripping wings thereon configured to assist in rotation of the sheath, one of the plurality of gripping wings having one or more indicators thereon configured to indicate a direction of the fixed non-zero angle, the one or more indicators comprise a plurality of ribs;
    a linkage having distal and proximal sides, the distal side of the linkage being configured to removably operably couple to the proximal end of the sheath, the linkage having a plurality of entry lumens on the proximal side thereof and a single exit lumen on a distal side thereof, the linkage being configured to merge the plurality of entry lumens into the single exit lumen, the linkage having only the single exit lumen on the distal side thereof; and
    an imaging device including a handle and an elongate imaging member extending distally from the handle;
    wherein the sheath and the linkage are configured to create an imaging path for the elongate imaging member and a fluid path for fluid from the plurality of entry lumens of the linkage, through the single exit lumen of the linkage, and into the single lumen of the sheath when the distal side of the linkage is operably coupled to the proximal end of the sheath; and
    wherein the linkage is configured to operably couple to the sheath to prevent axial translation and to allow axial rotation between the sheath and the linkage.

2. The system of claim 1, wherein the sheath and the linkage are configured to create a fluid seal therebetween when the sheath and the linkage are operably coupled, and the linkage and the imaging device are configured to create a fluid seal therebetween when the elongate imaging member is inserted along the imaging path.

3. The system of claim 1, wherein the sheath and the linkage are configured to create an imaging path for the elongate imaging member, a fluid path for liquid, and a surgical instrument path for a surgical instrument from the plurality of entry lumens of the linkage.

4. An imaging system, comprising:
a sheath having a distal end configured to allow imaging therethrough, a proximal end, and only a single lumen extending between the distal and proximal ends, the sheath having an angled distal portion that is angled at a fixed non-zero angle relative to a straight proximal portion of the sheath, the straight proximal portion extending along a longitudinal axis of the sheath, the sheath having a plurality of gripping wings thereon configured to assist in rotation of the sheath, one of the plurality of gripping wings having one or more indicators thereon configured to indicate a direction of the fixed non-zero angle, the one or more indicators comprising one or more surface features, the one or more indicators comprising a plurality of indicators, the plurality of indicators comprising a plurality of raised surface features, the plurality of raised surface features comprising a plurality of ribs;
a linkage having distal and proximal sides, the distal side of the linkage being configured to removably operably couple to the proximal end of the sheath; and
an imaging device including a handle and an elongate imaging member extending distally from the handle;
wherein the sheath, the linkage, and the imaging device are removably engageable with each other.

5. The system of claim 4, wherein the plurality of indicators are positioned on each side of the gripping wing.

6. The system of claim 4, wherein the plurality of indicators are configured to be identified through physical touch of a user.

7. The system of claim 4, wherein the gripping wing having one or more indicators thereon is visually distinct relative to the other wings of the plurality of gripping wings.

8. The system of claim 4, wherein the plurality of gripping wings are positioned at 90 degree intervals around the sheath.

9. The system of claim 4, wherein the linkage has a plurality of entry lumens on the proximal side thereof and a single exit lumen on a distal side thereof, the linkage is configured to merge the plurality of entry lumens into the single exit lumen, and the linkage has only the single exit lumen on the distal side thereof.

10. The system of claim 9, wherein the sheath and the linkage are configured to create an imaging path for the elongate imaging member and a fluid path for fluid from the plurality of entry lumens of the linkage, through the single exit lumen of the linkage, and into the single lumen of the sheath when the distal side of the linkage is operably coupled to the proximal end of the sheath; and
wherein the linkage is configured to operably couple to the sheath to prevent axial translation and to allow axial rotation between the sheath and the linkage.

11. The system of claim 10, wherein the sheath and the linkage are configured to create a fluid seal therebetween when the sheath and the linkage are operably coupled, and the linkage and the imaging device are configured to create a fluid seal therebetween when the elongate imaging member is inserted along the imaging path.

12. The system of claim 10, wherein the sheath and the linkage are configured to create an imaging path for the elongate imaging member, a fluid path for liquid, and a surgical instrument path for a surgical instrument from the plurality of entry lumens of the linkage.

13. The system of claim 10, wherein the linkage is configured to engage the handle of the imaging device when the elongate imaging member is inserted along the imaging path to prevent relative rotation or axial translation between the linkage and the imaging device.

14. The system of claim 9, wherein the distal-most end of the single exit lumen of the linkage has a cylindrical distal portion configured to be received within the sheath when the sheath and the linkage are engaged.

15. The system of claim 14, wherein the sheath has a rotatable seal disposed in a proximal portion thereof and the distal-most end of the single exit lumen of the linkage is configured to extend through the rotatable seal of the sheath when the sheath and the linkage are engaged such that a fluid seal is created therebetween.

16. The system of claim 4, wherein the distal end of the sheath is open such that fluid and a distal end of the elongate imaging member are extendable distally therefrom.

17. The system of claim 4, wherein the linkage and the sheath are configured such that, when the linkage is coupled to the sheath and the elongate imaging member extends along an imaging path formed through the linkage and the sheath, a distal-most end of the elongate imaging member is physically incapable of extending distally beyond the distal end of the sheath.

18. The system of claim 17, wherein the elongate imaging member is more flexible relative to the sheath such that the elongate imaging member is configured to bend at the fixed non-zero angle of the angled distal portion of the sheath when the elongate imaging member extends along the imaging path, and a distal end of the elongate imaging member is configured to obtain images while being oriented at the fixed non-zero angle of the angled distal portion.

* * * * *